United States Patent [19]

Fuller, II et al.

[11] Patent Number: 5,496,263
[45] Date of Patent: Mar. 5, 1996

[54] ANKLE STABILIZATION SYSTEM

[75] Inventors: Hadwen C. Fuller, II, Parish, N.Y.; Anthony H. G. Bell, Laguna Niguel, Calif.; Lutz Biedermann, VS-Villingen, Germany; David M. Rodgers, Mission Viejo, Calif.

[73] Assignee: Ascent Technologies Group, Inc., Parish, N.Y.

[21] Appl. No.: 775,186

[22] Filed: Oct. 11, 1991

(Under 37 CFR 1.47)

[51] Int. Cl.⁶ ...................................................... A61F 5/00
[52] U.S. Cl. .............................................. 602/27; 602/23
[58] Field of Search ................................. 602/5, 16, 23, 602/27

[56] References Cited

U.S. PATENT DOCUMENTS

| | | |
|---|---|---|
| 3,593,342 | 7/1971 | Niebauer . |
| 3,834,377 | 9/1974 | Lebold ...................... 602/27 |
| 4,517,968 | 5/1985 | Greene et al. ............... 602/27 |
| 4,587,962 | 5/1986 | Greene et al. ............... 602/27 |
| 4,628,945 | 12/1986 | Johnson, Jr. . |
| 4,693,239 | 9/1987 | Clover, Jr. . |
| 4,771,768 | 9/1988 | Crispin . |
| 4,834,078 | 5/1989 | Bierdermann . |
| 4,934,355 | 6/1990 | Porcelli . |
| 4,962,760 | 10/1990 | Jones ........................ 602/27 |
| 4,977,891 | 12/1990 | Grim . |

FOREIGN PATENT DOCUMENTS

| | | |
|---|---|---|
| 0416913A3 | 3/1991 | European Pat. Off. . |
| 8707498 | 12/1987 | WIPO . |

OTHER PUBLICATIONS

1989—Product literature by Aircast® relating to pneumatic braces.
1988—Product literature by Aircast® relating to ankle braces.
1989—Product literature by Royce™ Medical Products relating to a lightweight gel ankle brace.
Product literature by AllMed, Inc. relating to Gelcast™ ankle brace.
Product literature by Surefit Orthopedics™ relating to various orthopedic devices.
1987—Product literature by Donjoy® relating to a motion walker and ankle ligament protector.
1988—Bracing catalog by Donjoy®.
1988 & 1990—Product literature by Swede-O-Universal® relating to various ankle supports.
Product literature by McDavid™ Sports Medical Products relating to laced ankle braces.
Product literature by Physical Support System, Inc. relating to an ankle stabilizer.
Advertisement by Cramer relating to an ankle stabilizer.
Advertisement by T'Brace Corp. relating to lace-up ankle brace.
Advertisement by Mueller® relating to an ankle brace.
1990—Advertisement by Omni Scientific, Inc. relating to duo-loc ankle support.

(List continued on next page.)

*Primary Examiner*—Linda C. M. Dvorak
*Attorney, Agent, or Firm*—Knobbe, Martens, Olson & Bear

[57] ABSTRACT

A system for stabilizing the injured ankle of a user has an ankle brace with an upper calf member hingedly connected to a lower foot member, and a plurality of reinforced areas for strengthening and supporting a region around the talus bone. The reinforced areas are located above and below the hinge, or in the proximate vicinity of the ankle and talus bone. The hinge is located on an outwardly bowed cup-shaped portion of the ankle brace for comfortably receiving the mallseli of the user. The upper member includes a pair of arcuate elements slidable with respect to one another to adjust the opening formed thereby for various calf sizes. The lower member is designed to reduce stiffness in areas such as the front of the foot. Several straps are provided to securely couple the upper member and lower member to the user. Inner pads and tapered edges of the structural members reduce abrasion of the ankle brace against the user.

7 Claims, 5 Drawing Sheets

OTHER PUBLICATIONS

Product literature by Active Ankle Systems, Inc. relating to an ankle orthosis.

Product catalog by Sport Supports® relating to various ankle supports.

Product literature by Sport Supports® relating to Allsport and Kallassy ankle supports.

1989—Product literature by Three–D Orthopedic, Inc. relating to a stirrup ankle brace.

1989—Product literature by Donjoy relating to a Dynasport™ protective bracing.

Product literature by Orthomedics® relating to an ankle brace and orthosis.

Advertisement by Becker Orthopedic Appliance Co. relating to a double flexure ankle joint system.

Solicitation letter by Beverly Hills Prosthetics Orthotics, Inc. relating to an ankle orthosis.

1987—Product literature by Zinco Industries, Inc. relating to various ankle support product.

Advertisement by Pro Orthopedic Devices relating to an ankle brace.

Advertisement by Arthrogo™ relating to an ankle brace.

1990—Product literature and solicitation letter by Euroscand, Inc. Medical Division relating to an ankle brace.

1990—Product literature by All Orthopedic Appliances™ relating to Quick Fit Ankle Brace.

1989—Article relating to an Ankle Stabilizing Orthosis (ASO™) by Medical Specialists, Inc., vol. 24, No. 3, p. 277 of *Athletic Training*.

1988—Article entitled "Trainers Debate Merits of Ankle Braces and Tape", Jul./Aug. 1988 volume of *Sports Medicine*.

1989—Article entitled "A Stabilizing Effect", Aug. 1989, vol. 1, No. 4 of *College Athletic Management*.

1984—Article entitled "An Ankle Owner's Manual, A Guide to Common Ankle Injuries", published in 1984 by Patient Information Library™.

1983—Article entitled "Common Ankle Injuries in Sports," published by Charles Roland, M.D., vol. 5, No. 9, Sep. 1983 issue of *Family Practice Recertification*.

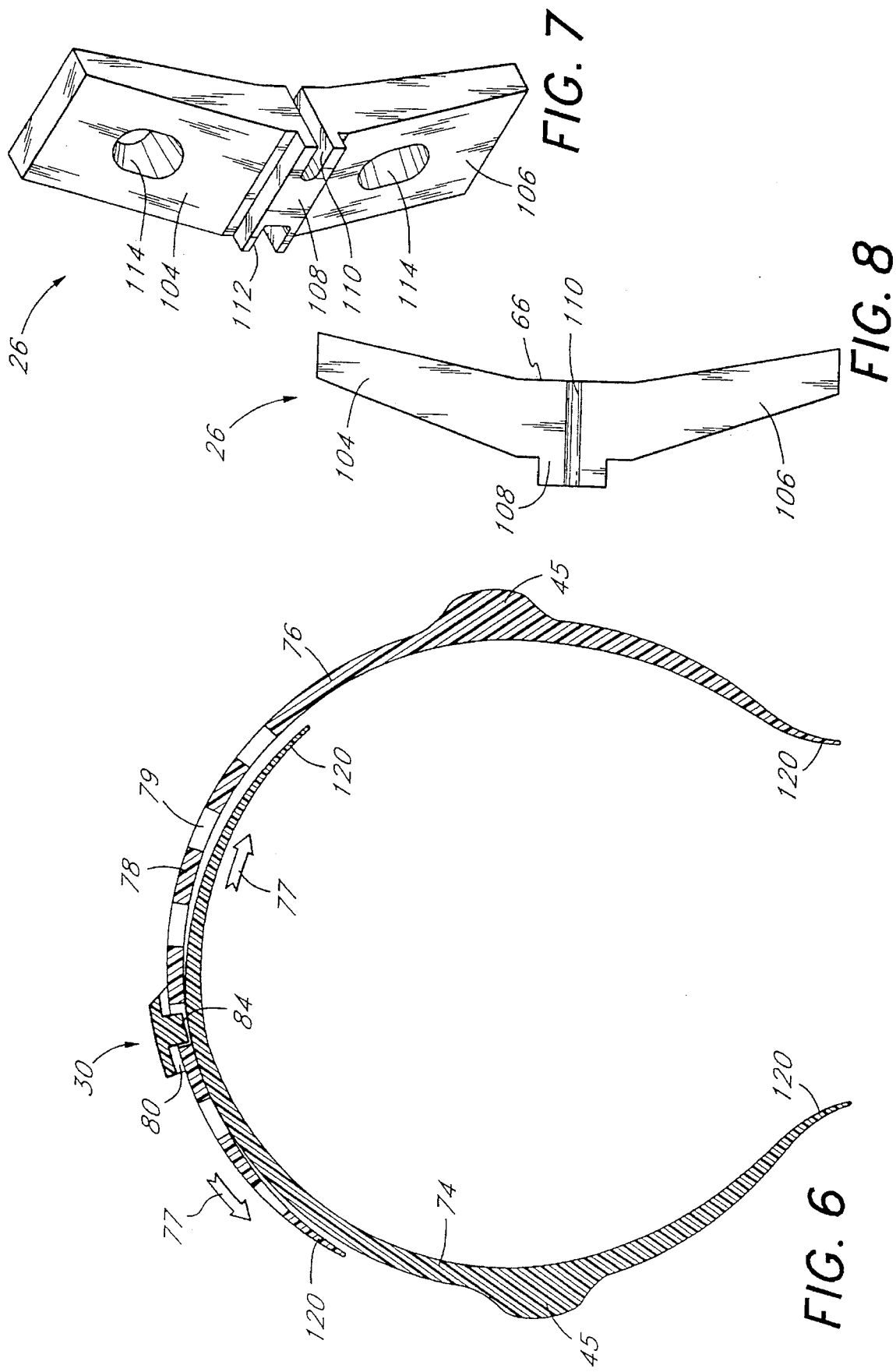

5,496,263

ANKLE STABILIZATION SYSTEM

FIELD OF THE INVENTION

The present invention relates to an orthosis designed to provide stabilization to the tarsal joint, comprising: an adjustable two-piece calf module consisting of two side members with adjustable latches and straps such that the module adjustably conforms to and partially embraces the shank portion of the lower leg; an ankle module with adjustable straps which secures and embraces the foot by conforming at least partially to the heel and metatarsus; a rigid skeletal frame on and within said calf module and ankle module wherein the frame substantially coincides with the human skeletal structure for proper support and adaptation of movement; and a joint connecting said calf module and said ankle module comprising an elastomeric member that provides flexibility in at least one direction while limiting or restricting movement in undesired directions.

BACKGROUND OF THE INVENTION

In recent years, there has been a rapid growth in the popularity of sports and recreational activities amongst all age groups. Leisure and recreation has become an important aspect of a person's lifestyle. Concomitantly, there has been an increasing number of "weekend" athletes participating in gyms, tracks and courts, etc.

Injuries to the ankle joint or sprains are commonly experienced by athletes and individuals who participate in a variety of different recreational sports, i.e., tennis, soccer, basketball or racquetball, as well as other activities. Damage to ligaments are especially common and can be quite painful causing the injured person to be unable to walk or run properly for a period of time. Because these injuries have become widespread, there is a need for an affordable orthopedic device designed to provide support to the ankle joint so as to prevent injury or allow the injured person to walk or even to continue his or her recreational activity.

In the past, athletes have relied on ankle tape or wrapping to provide ankle support in the event of injury thereto or to prevent injury. Ankle wraps and tapes, however, are difficult to self-apply and typically provide limited support to the ankle while constricting free movement. In addition, only trained individuals know how to properly apply tape to the ankle such that proper support is rendered. The typical weekend athlete therefore is often unable to obtain proper taping.

Custom-fit orthopedic devices with rigid stabilizing receptacles and a hinge to allow free movement in the appropriate direction have also become available. One disadvantage of custom-fit devices, however, is just that: they must be custom fit by a trained orthotist. This adds substantially to the cost of the device. Recreational athletes or sportsmen may be unwilling to pay for a customized ankle brace when their activities are limited, or when they may only need the ankle device during the recovery period, which in many cases may last only a few weeks. Thus, many recreational athletes and sportsmen may go without an ankle brace, and either risk further and permanent injury to the ankle by continuing activity without adequate support for the ankle, or abstain completely from activity until the ankle is healed. The need for a reasonably inexpensive yet adjustably fitted, off-the-shelf, ankle brace is therefore apparent. There is also a need for an improved ankle stabilization system, whether or not custom-fitted.

SUMMARY OF THE INVENTION

The present invention represents a substantially improved, adjustable, ankle stabilization system. The advantage of the ankle brace of the present invention is that it need not be custom fit, thereby reducing the cost and inconvenience associated with previous custom fit ankle braces. Furthermore, the present ankle brace can be marketed as an off-the-shelf product, being available in various standard sizes which can comfortably fit the lower limb structure of virtually all individuals. This product can also be economically manufactured and sold in a wide variety of stores, thus making it easily available to the consumer.

It should be pointed out that the principles of the present invention apply equally to custom-fit ankle braces, and other types of ankle orthopedic devices. Thus, the ankle stabilization principles of the present invention are not limited to an adjustable, universally-fitting device as illustrated and described herein; although, these principles of adjustability are within the scope of the present invention.

The stabilization system of the present invention comprises an ankle brace having an ankle module and a calf module connected to one another by a hinge device. These two modules, in cooperation with the hinge, provides superior tarsal support, particularly for the ankle bones (or tarsal joint) and the talus. That is, many ankle injuries are incurred in the ligaments which bind the tarsal and lower leg bones together, the most significant of which, for purposes of this discussion, are the talus, the navicular (located just anterior and medial of the talus), the malleoli (the distal bulbous ends of the tibia and fibula lower leg bones and what laymen usually refer to as the ankle bones), and the calcaneus or heel. The top portion of the talus, which is the highest tarsal bone, fits between the malleoli and moves between them like a hinge. If this movement is over-extended sideways, such as by inversion or eversion, the tarsal ligaments are stretched or torn and a sprained ankle results. The malady is not uncommon, especially when one considers the multi-directional flexibility of this tarsal joint and the leverage placed upon it by the legs. Furthermore, the heel or calcaneus, being somewhat rounded and relatively narrow, is not an inherently stable anatomical structure.

Thus, embodied in the ankle brace of the present invention is a stabilization and support system for the talus and the major bones which surround it to form the tarsal joint. The structure of the present invention provides improved taloric support by means of a control system comprising: (i) a direct taloric control device; (ii) a subtaloric control device; and (iii) a superior taloric control device.

The direct taloric control device is provided in the form of reinforcement areas located on both sides of the U-shaped ankle module of the present ankle brace. Each direct taloric reinforcement area directly braces one side of the talus in the region of its joinder with a malleolus. Each reinforced area is also securely fastened to the hinge mounting bracket on the ankle module, which also provides reinforcement and stabilization to the talus. The reinforcement area is somewhat triangular in shape and, when combined with the essentially rectangular reinforced area comprising the mounting bracket, mimics the shape of the tarsal joint. Thus, the talus and its critical hinging action with the malleoli is provided with improved support by means of this direct taloric control device.

The sub-taloric control device is comprised of a reinforced area located on the ankle module below the direct taloric control device reinforcement area. This reinforcement area is located along the lower longitudinal side regions of the ankle module and extends to the bottom surface of the ankle module below the arch of the foot. On each side of the module, this subtaloric reinforcement area engages the foot in the subtarsal region, and provides excellent support and stabilization for the tarsal region.

The superior taloric control device comprises an essentially vertical support member or pillar incorporated into the calf module on each side thereto. This pillar is aligned approximately with the lower leg bones (the tibia and the fibula) and provides support to the tarsal joint in the area above the talus/malleoli interface. This alignment provides the ankle brace system with an improved adaptation of movement of the ankle to the brace, as the skeletal features of the lower limb coincide with those of the superior taloric control device.

At its distal end, the pillar is provided with an upper hinge mounting area for joining the calf module to the ankle module by means of the hinge described below in more detail. The pillar is constructed with a recessed area at the distal end, into which the elastomeric hinge device is inserted and attached. This superior taloric control device is comprised of a reinforcement member, fitted to the calf, which in connection with the reinforcement of the direct and subtaloric devices, controls the movement of the talus, thereby inhibiting overextension. The rigid pillar structure of the calf module also allows the non-rigid, flexible body of the module, and in particular, the peripheral edges of the module, to be thinner and flared away from the user's skin so that it is more flexible and does not dig into the user's soft tissue. This feature, which is also exhibited in the ankle module, allows the user more comfort and extended wear.

Accordingly, these various taloric control devices provide excellent support and stabilization to all facets of the tarsal joint, and particularly to the articulations of the talus. It can be said that they form the skeleton of the ankle brace of the present invention.

This skeletal design also advantageously permits the flexible material, from which the non-skeletal portions of the modules are constructed, to be relatively thin and flexible. As such, the material conforms more closely to the contours of the shank and ankle areas. The material can also be tapered away along its periphery from the wearer to prevent the edges of the modules from biting into or cutting the soft tissue of the wearer.

In addition, the ankle module is provided with a pair of straps which enhance the stabilization performance of these taloric control devices. An anterior support strap is located just in front of the direct taloric device and is relatively wide in order to provide maximum comfort and control. This strap pulls the sides of the ankle module together in order to cause them to conform snugly and securely to the wearer's foot, thereby enhancing the performance of the direct- and sub-control devices. This anterior strap is located on the upper region of the ankle module, so that it can wrap across the top of the navicular region of the foot.

The ankle module is also provided with a posterior support strap located to the rear of the direct taloric control device. Like the anterior support strap, this support strap allows the ankle module to be snugly fitted to the wearer's foot along the sides thereof, and prevents the heel portion from lifting upon use.

It should be noted that the anterior portion of the ankle module is somewhat truncated, so as to not extend too far forward and interfere with the metatarsal region or plantar arch of the foot. Because these regions of the foot relate less directly to taloric control, the truncation of the ankle module has no detracting effect from the control aspects of the device. To the contrary, the truncation enhances the adjustability of the present ankle brace, as the ankle module does not engage the metatarsal region, which varies widely from one person to another person.

On the other hand, the upper regions of the ankle module extends relatively far in the longitudinal direction in order to engage the entire tarsal area and improve taloric control. The support straps of the ankle module are fastened to the ankle module in this region in order to permit the taloric control devices to be secured snugly to the foot and to maximize the effect of the structural rigidity of the control devices.

Being fastened to the upper non-reinforced regions of the ankle module, the straps are designed such that the naturally flexible material of the ankle module can be tightened to wrap around the tarsal area. This flexibility on the periphery is advantageously permitted as a result of the support provided by the reinforced areas as well as the straps; the non-reinforced areas of the ankle module need not be rigid to maintain their wrap-around support. At the edges, this flexible material can be slightly turned away from the foot of the wearer to prevent the edge of the ankle module from digging into the soft tissue of the wearer. Furthermore, the straps engage the periphery of the talus, both anteriorly and posteriorly, thereby securing the module to the wearer's foot and tarsal area.

The anterior and posterior support straps also provide an important adjustment mechanism in connection with the ankle module. Because of differences in foot anatomy, as explained above, it may be desirable to adjust the longitudinal position of the foot, and more particularly, the ankle, with respect to the ankle module so that the malleoli are received properly with the best possible fit. Because of the U-shaped nature of the ankle module, this longitudinal adjustment is possible in cooperation with the anterior and posterior straps. That is, the foot can be adjusted slightly forward or rearward so that the malleoli are aligned in the most comfortable position within the cup-like areas of the brace. Then, the straps of the ankle module may be secured so that the ankle is securely retained in this position. It should be noted that the invention is best suited to be worn with a pair of shoes, as the shoes provide additional support to the tarsal region and hold the brace in place to prevent movement of the ankle module with respect to the user's foot.

In addition, it is well known that the two bones of the malleoli are not symmetrically aligned as they are offset both vertically and longitudinally. Also, their degree of orientation and protrusion varies from person to person. The large bony structure of each malleolus is not covered by a significant amount of skin or muscle, thus leaving open a potential for irritation and injury caused by friction with the ankle brace.

The present invention provides a pair of concave cup-like areas for receiving the malleoli bones without causing friction or abrasion thereto. These cup-like areas are arranged on opposite sides of the present ankle brace, so that they cover each side of the ankle joint. The cup-like areas are located near the region of the hinge elements connecting the calf module to the ankle module. However, as explained above, the centers of these cup-like areas are offset vertically and longitudinally so as to conform generally with the anatomical arrangement of each malleolus. This design, therefore, compensates for the various human structural differences in this important region of the ankle.

These cup-like areas are formed through a cooperation in the lower distal region of the calf module and the upper region of the ankle module, both of which bow slightly in an exterior direction. Moreover, the elastomeric hinge also exhibits a slight concave configuration so that the hinge does not rub the malleoli area. Although the cup-like areas are slightly concave in order to avoid the malleoli, a snug fit with the adjacent areas is still achievable by means of the padding and the two support straps of the ankle module and the lower strap of the calf module, as described below in more detail. Thus, the present invention provides excellent taloric control and at the same time accommodates most anatomical differences in malleoli placement.

The present invention is also provided with an improved proprioception sensitivity by its being able to control the talus without unduly restricting the calcaneus. The ankle module of the present invention is provided with an open heel design; the upper and exterior regions of the calcaneus are left free and unrestricted. Furthermore, the lower regions of the ankle module are cut forward in order to provide maximum ground contact for the heel. The posterior support strap on the ankle module, as explained above, is also situated at the upper regions of the ankle module, such that the straps wrap around the upper region of the calcaneus, leaving the lower region free and unrestricted. This design provides excellent taloric control without inhibited proprioception, which allows the body to balance itself.

There are other important advantages of the present invention. For example, it provides nearly as much comfort and contour fitting as the customized ankle braces, without the additional cost of customization. This invention is suited for off-the-shelf use by recreational athletes and sportsmen who only need the ankle brace as a temporary means of supporting their ankle to prevent inversion and eversion of the ankle. Because the invention does not have to be customized, and any one of several sizes are designed to adjustably fit virtually any contour of any human calf and foot, the cost of this invention to the consumer is more reasonable. Therefore, a greater number of individuals who are inflicted with ankle injuries or otherwise desire ankle support will be able to afford this unit and obtain the support needed for their ankle to continue their recreational activities.

One significant feature of the invention is the two-piece calf module, which consists of a latch system adjustably locking the module into position around the contours of the lower leg and calf. The calf module comprises two side members which are adjustably connected on a vertical side by two or more adjustable latches. The two side members overlap and are integrated with the latch mechanism such that the two members act as one rigid piece. This advantageously provides the adjustability of a two-piece calf module, with the strength and rigidity of a one-piece module. The side members are also connected on the open vertical side by two adjustable, stretchable and wrappable strip fasteners. The stretchable strip fasteners secure the calf module to the shank and provide a more sensitive adjustment of a fine tuning nature.

The two wrappable and adjustable straps encircle the lower leg such that they can be adjusted to allow the module to properly fit the user's lower leg and calf. In one embodiment, the straps are counter-rotated so that each strap tightens in the opposite rotational direction, which provides for multi-directional tightening for a more consistent fit and wear. The wrappable straps are also made stretchable with an elastic material, thus allowing for unrestricted flexion and extension of the gastrocnemius within the module. The fasteners can also be fastened directly to slots in the rigid vertical pillars on the side of the calf modules so that the straps are directly connected to the structural member of the calf module, which ensures a proper fastening of these members at their strongest points. The fasteners can also be made of a VELCRO® material.

The present invention also encompasses a unique calf module sizing system which enhances the ability of the present ankle brace to be sold as an off-the-shelf, standard size product. In accordance with this system, it has been discovered that a certain range of calf module parameters loosely correspond to standard shoe sizes for most individuals. Thus, the adjustable dimensions of the calf module are designed to fall variably within given ranges for a particular shoe size. This allows the present invention to be conveniently marketed to the consumer at an easily affordable price.

The invention also includes a unitary elastomeric joint member or hinge connecting the calf module to the ankle module, providing flexibility in at least one direction while restricting movements in undesired directions. The hinge is provided with a configuration whose moment of inertia restricts torsion, while the overall configuration of the hinge permits flexibility in a rotational direction around the horizontal axis of the joint. In addition, the hinge is placed in a neutral position, such that the axis thereof matches the axis of the malleoli joint. The joint member can also be made such that flexibility is enhanced in one or more directions and is limited in others.

The joint connecting members are also advantageously rectangular in shape, fitting tightly within the rectangular shaped recesses in the connecting areas of the calf and ankle modules. This rectangular fit serves to provide a rigid connection which resists torsional and rotational movement in and around the joint. Due to this torsion-restrictive fit, the movement of the dorsal/plantar flexion is properly controlled by the elastomeric joint itself. The forces applied by the user are properly distributed to and throughout the rigid structure of the calf and ankle modules.

The ankle module and calf module also contain padding members on the inside portion to provide comfort to the user by providing cushioning around the ankles, the malleoli, the gastrocnemius and the soleus. In particular, the padding immediately above and below the hinge serves to elevate the hinge away from the malleoli so that the hinge does not come in contact with the malleoli.

In summary, the ankle brace of the present invention provides both an improved tarsal joint stabilization system and an adjustable brace which can easily accommodate the anatomical differences among wearers.

BRIEF DESCRIPTION OF THE DRAWINGS

FIG. 6 is a cross-sectional view of the calf module taken through a latch mechanism of the present invention illustrating its adjustable features;

FIG. 7 is a perspective view of the hinge of the present brace which connects the calf module to the ankle module; and FIG. 8 is a side view of the hinge of FIG. 7 illustrating its generally concave inner surface and its general configuration which inhibits torsion.

DETAILED DESCRIPTION OF THE INVENTION

Figure 1:
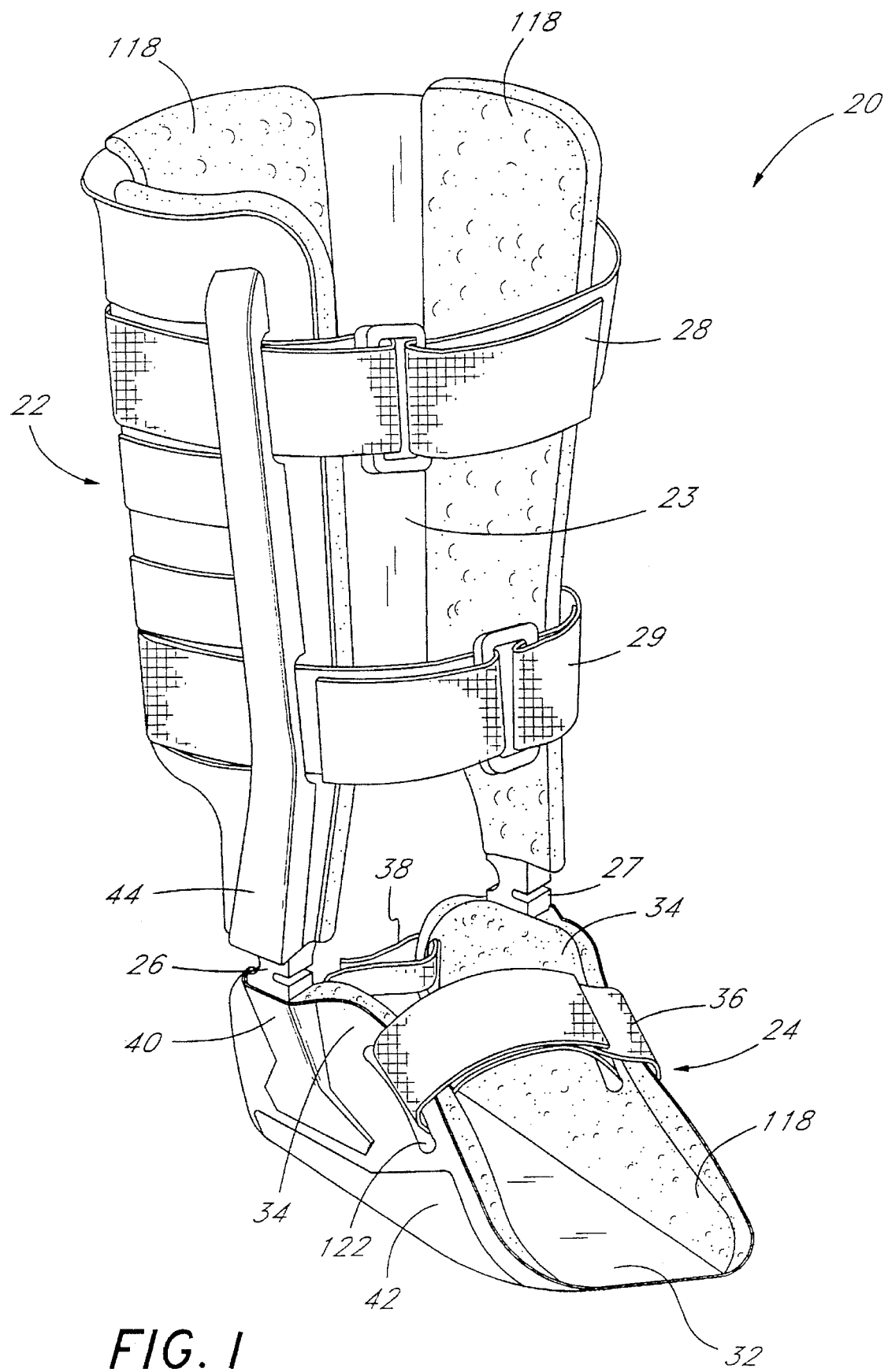
FIG. 1 is a perspective view of the ankle brace of the present invention.

Referring to FIG. 1, there is shown a perspective view of the ankle brace 20 of the present invention. FIG. 1 illustrates the components of the present brace 20, including a calf module 22, an ankle module 24, and hinges 26, 27 which join the two modules together in a flexible fashion explained below in more detail.

Figure 4:
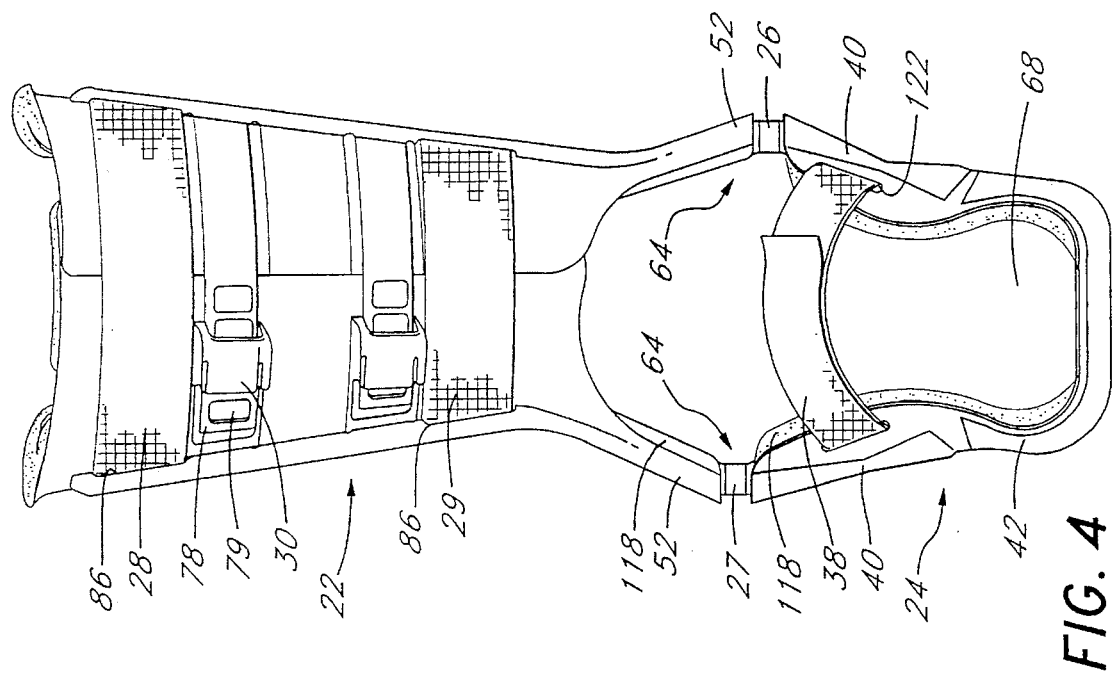
FIG. 4 is a rear view of the present brace illustrating its improved proprioception capabilities.

The calf module 22 is somewhat cylindrical in shape and engages the muscular region of the lower leg, but avoids interference with the calf muscle (or gastrocnemius). The calf module 22 almost completely surrounds the lower leg, providing only a vertical opening 23 in the front along the shin area. The calf module 22 is comprised of a two part overlapping construction which is retained in position by a pair of latches 30 (FIG. 4). Additionally, the calf module 22 is drawn together by a pair of straps 28, 29 which help to secure it in position and provide adjustability. The important adjustability advantages of the present invention as particularly exemplified by the calf module 22 are explained below in more detail in connection with FIG. 5.

The ankle module 24 is generally U-shaped and is comprised of a base portion 32 or sole and two upwardly extending sides 34. The sides 34 are drawn together in order to conform to the configuration of the user's foot by means of two adjustable straps—an anterior support strap 36 and a posterior support strap 38, which can be of a VELCRO®-type material. Thus, this configuration provides a wide degree of adjustability while at the same time providing excellent support for a tarsal joint 54 (FIG. 2a), as explained below.

Thus, it can be seen from FIG. 1 that the ankle brace 20 of the present invention surrounds the tarsal joint 54 with supporting structure drawn together snugly by various support straps. This arrangement provides structural support to the tarsal joint 54 without undue or tight pressure. At the same time, one of the major advantages of the present ankle brace 20 is that it is highly adjustable. The brace 20 can be constructed from a variety of materials which provide rigidity and support for the tarsal joint 54. Preferably, the major components of the calf and ankle module are constructed from an injection molded thermo-plastic material.

The structural support and stabilization to the tarsal region 54 is provided in the present invention by a plurality of cooperative taloric control devices, two of which are located on the ankle module 24 and one of which is situated directly above at the lower, distal region of the calf module 22 and extending upward thereto, as illustrated in FIG. 1. It should be noted that, in each case these control devices comprise a pair, one located on either side of the brace 20. Thus, for ease of illustration and with particular reference to FIG. 2, only a single control device will be described; however, it will be understood that this explanation applies to both members of the control device pair. Likewise, only one hinge 26 will be described with the understanding that there is an identical hinge 27 disposed on the opposite side of the ankle brace 20.

Figures 2, 2A:
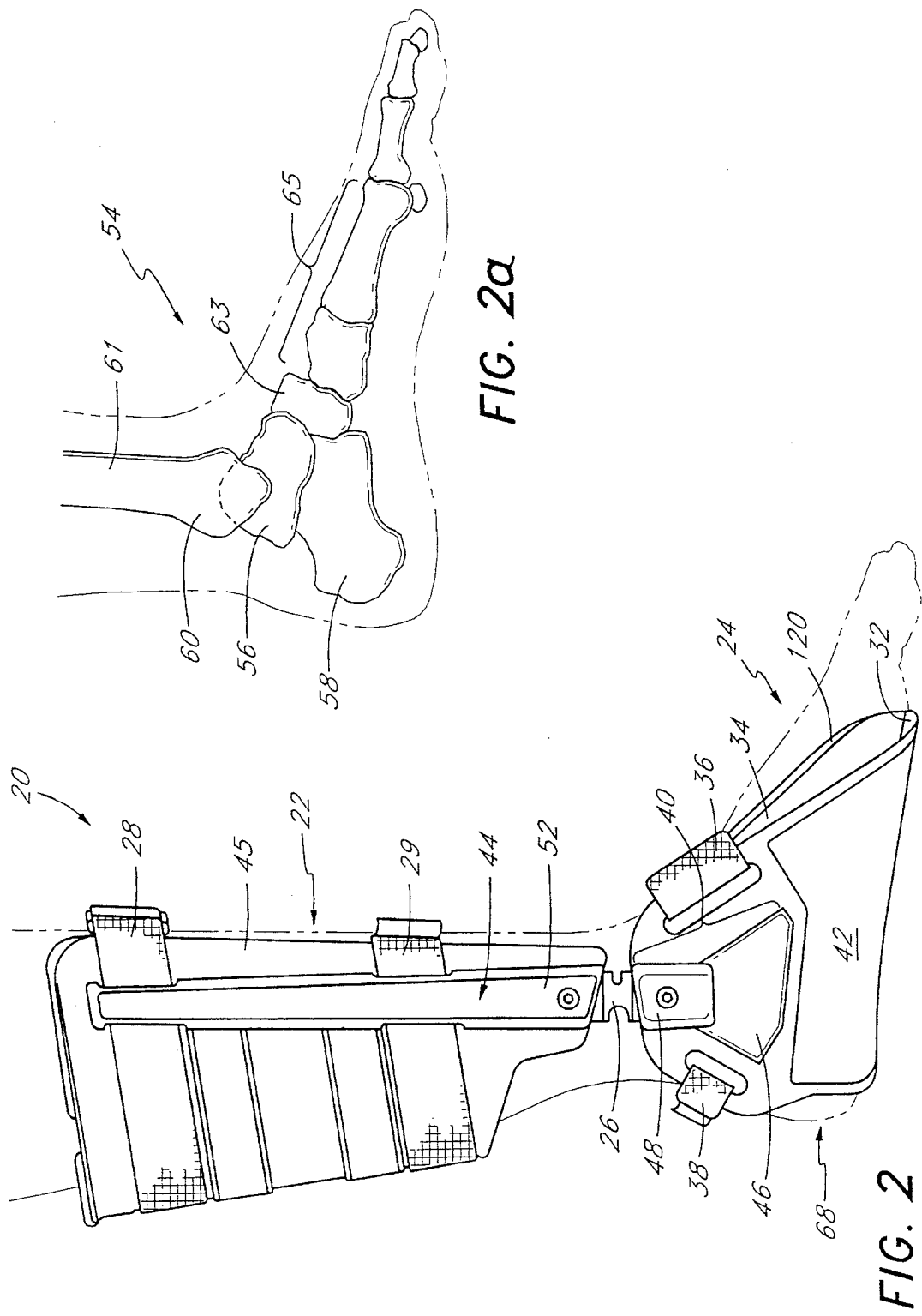
FIG. 2 is a side view of the present ankle brace illustrating the typical positioning of the brace on the foot of a wearer.
FIG. 2a is a side view of the human foot from the medial side showing the various tarsal bones thereof.

With reference to FIG. 2a, a skeletal representation of the lower leg and foot bones as viewed from the instep is depicted. The particular bones of the tarsal region 54 to which the taloric control devices correspond may be easily seen, and thus a detailed description is helpful. A tibia bone 61 extends down from the knee region (not shown) to a location directly above the tarsal region 54. A fibula 62 (not shown) runs parallel and proximate to the tibia 61 on the lateral side of the leg. The extreme ends of both the tibia 61 and fibula 62 bones have a bulbous end known as malleoli 60, or what are commonly referred to as the ankle bones. Directly below the malleoli 60 is a talus bone 56. The talus 56 sits approximately on the anterior section of the calcaneus bone 58, which is more commonly known as the heel. Anterior of the calcaneus 58 and the talus 56 is a navicular bone 63, and slightly farther forward are metatarsal bones 65.

FIG. 2 illustrates the placement of these taloric control devices, including a direct taloric control device 40 located in the upper and central region of one side 34 of the ankle module 24, a sub-taloric control device 42 located along the lower longitudinal regions of the ankle module 24, and the superior taloric control device 44 located in the lower distal region of the calf module 22 and just above the hinge 26. These control devices reinforce the ligaments which support the talus 56 in its position relative to the critical bones with which it mates. These control devices work together in a cooperative fashion to virtually surround the talus 56 in support of the ankle joint so as to inhibit over-extension and promote healing.

Referring again to FIG. 2, the direct taloric control device 40 is comprised of a reinforced or strengthened area located on either side 34 of the ankle module 24. This reinforced area provides extra strength and rigidity to the ankle module 24 so as to stabilize the tarsal joint 54, and in particular to carefully control the movement of the talus 56. It should be pointed out, in connection with the overall principles of the present invention, that the purpose of the present brace is not to prevent movement of the ankle joint, but rather to securely control it and prevent over-extension by means of inversion or eversion. Thus, one of the advantages of the present invention is that the brace can be worn while the wearer is participating in normal physical activities, thereby preventing injury, allowing the joint to heal, and permitting freedom of movement to the wearer.

The direct taloric control device 40 is comprised of a generally triangular reinforcement area 46 and an upper hinge mounting bracket 48 which is also reinforced and made relatively rigid. Thus, in combination with the reinforced superior taloric control device 44 and the hinge 26, the direct control device 40 provides direct support to the talus/malleoli interface.

The subtaloric control device 42 is located just below the direct taloric control device 40 and is also comprised of a reinforced area on the side 34 and bottom 32 of the ankle module 24. This area is generally rectangular in configuration, and is aligned generally along the talus/calcaneus interface. This reinforcement area 42 is subtaloric in the sense that it strengthens and supports the base upon which the talus 56 rests, namely, the calcaneus 58 and navicular bones 63.

The superior taloric control device 44 is comprised of a generally vertical reinforcement member 52 located at the lower distal end of the calf module 22, as shown in FIG. 2.

This reinforced area 52 continues vertically in an upward direction to form a relatively rigid center member or pillar 45 on each side of the calf module 22. This superior taloric control device 44 engages the tibia 61 and fibula 62 region on each side of the leg for stability and assists in controlling the movement of the talus 56. Thus, these taloric control devices provide excellent support and control for the various articulations of the talus 56.

In connection with this freedom of movement, the hinges 26, 27 of the present invention provide an important advantage by permitting the talocrural articulation to move about a single axis, but inhibit torsional movements which can lead to loss of control and possible inversion or eversion.

Figure 3:
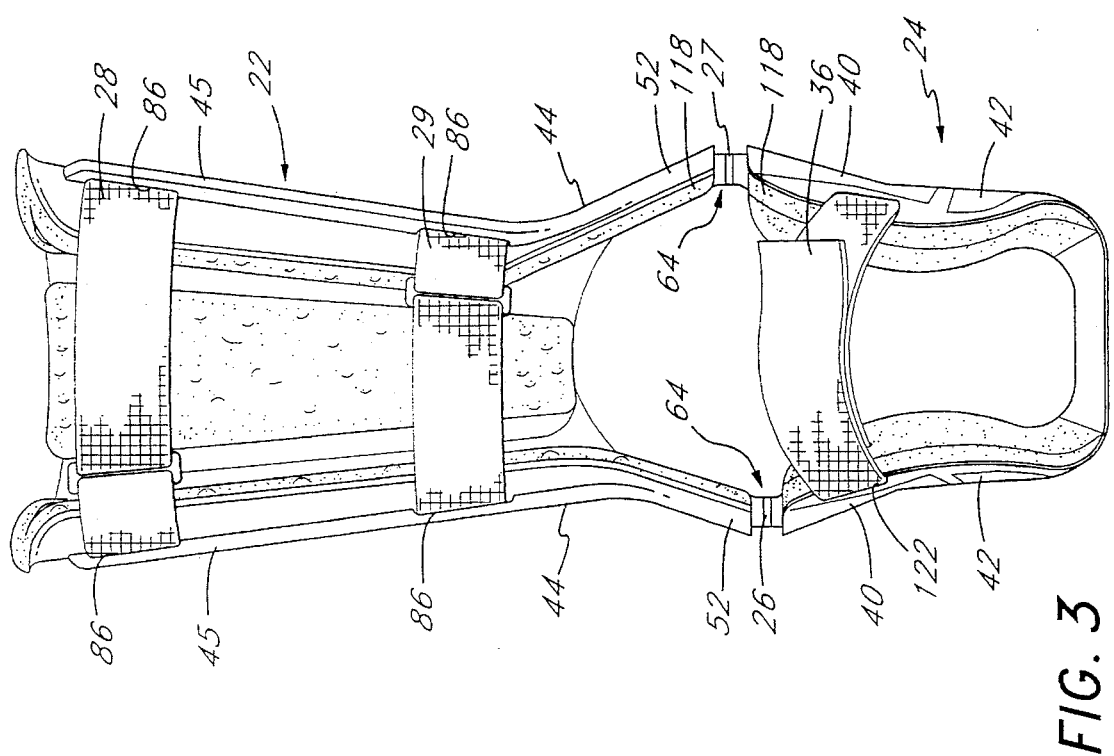
FIG. 3 is a front view of the present brace illustrating the generally U-shaped nature of the ankle module and the malleoli receptacles.

The ankle module 24, as shown in FIG. 2, comes with a pair of support straps, also as shown in FIGS. 3 and 4, to provide the important advantages of the present invention. The anterior and posterior support straps, 36 and 38, respectively, are located in the upper regions of the sides 34 of the ankle module 24, as best shown in FIG. 2. The other pair of support straps 28, 29 can be mounted on the side members of the calf module 22 through the vertical slots 86 in the rigid pillar members 45, as shown in FIG. 3. All of these support straps draw the components of the various taloric control devices together so that they snugly engage the foot of the wearer in order to provide support and stabilization.

Because of the conforming shape of the two modules, it is not necessary that they be drawn too tightly together since the structure of the modules provides adequate support. Thus, the present ankle brace 20 fits snugly and can provide control without placing pressure on the foot, which pressure restricts circulation and inhibits healing.

In this regard, as can be noted best from FIGS. 2 and 2a, the straps 36, 38 surround the tarsal joint area 54 rather than directly engaging it. In particular, the anterior 36 and posterior 38 support straps are positioned at the upper regions of the ankle module 24 so as to be peripheral to the anterior and posterior regions of the talus 56. These are relatively bony areas of the ankle where there is little soft tissue. On the other hand, these are important taloric control areas, which control is advantageously provided by the straps 36, 38.

In particular, the anterior support strap 36 is relatively wide, being approximately 1½ inches in width, in order to comfortably support the forward region of the talus 56. The posterior periphery of the talus 56 is less exposed and therefore requires a relatively narrow posterior support strap 38. Thus, in combination, various taloric control devices closely conform to the sides of the talus 56 and support its interface with the various surrounding bones, while the anterior 36 and posterior 38 support straps support the front and rear periphery of the talus 56. Accordingly, this important bone is stabilized.

Since the anterior 36 and posterior 38 support straps are located relatively high on the ankle module 24, the natural flexibility of the material from which the sides 34 of the module is constructed allows them to bend and flex as they are drawn by the straps 36, 38. Thus, the ankle module 24 is permitted to conform to the configuration of the ankle and heel areas of the user by means of the straps 36, 38.

The straps 28, 29, 36, 38 can be constructed from any suitable material which provides both adjustability and slight stretchability. Preferably, this material would be a VELCRO®-type fastener. Although such material is firm and strong and provides for an excellent support strap, it also provides approximately 15% stretchability. This is an important advantage of the present invention in that it prevents the straps from binding the foot too tightly, thereby cutting off circulation and inhibiting healing. In addition, as pointed out above, this stretchable feature in the straps permits controlled movement by the wearer.

It should be noted that the support straps 28, 29 on the calf module 22 can be mounted in opposite directions so that, when tightened, they provide counter-rotation to the shank. This prevents one support strap from exerting an excessive torque in one direction or the other on the shank. Furthermore, the calf module 22 is carefully designed with respect to its height so as to not interfere with the gastrocnemius muscle. Likewise, the lower portion of the calf module 22 is cut away, as illustrated in FIG. 2, so as to avoid interference with the Achilles tendon.

Another important advantage of the anterior and posterior straps, 36 and 38, respectively, is that they allow for longitudinal adjustment in the positioning of the foot within the ankle module 24. As evident from FIGS. 3, 4 and 5, the U-shaped nature of the ankle module 24 allows the foot to be adjusted to a variety of positions therein. Once the proper position has been determined, the anterior 36 and posterior 38 support straps secure the ankle module 24 in position with respect to the foot. This position is determined principally by the particular arrangement of the malleolus bone 60 on the tibia 61 and fibula 62 of the wearer. As noted above, these malleoli 60 are not symmetrical, nor does the ankle usually rotate about a true horizontal axis. Rather, the ankle exhibits a slight amount of pronation or supination during the movement of the wearer. These characteristics and the orientation and degree of protrusion of the malleoli 60 will vary from person to person. In addition, these bones are covered with only a thin layer of skin, thus leaving them vulnerable to friction and abrasion.

Accordingly, another important advantage of the present invention is the provision of cup-like malleoli receiving areas 64 formed on the sides of the present ankle brace 20. These cup-like areas 64 are best illustrated in FIGS. 3 and 4 and comprise areas which are somewhat concave in shape in the region of the opposing malleolus bones 60. It can also be noted from these figures that these cup-like areas 64 are offset vertically so as to conform more closely to the malleoli 60. The cup-like areas 64 are formed through the cooperation of the lower regions of the calf module 22 and the upper regions of the ankle module 24, both of which bow outwardly slightly. The interior surface 66 of the hinge 26 exhibits a slight inward taper and concave bend in order to accommodate the concavity of the area 64, as best seen in FIG. 8. In this regard, it should be noted that the hinges 26, 27 are non-overlapping, thus leaving the central portions of the cup-like areas 64 clear to house the malleoli 60.

Again, the anterior 36 and posterior 38 support straps of the ankle module 24 are situated close to but do not directly engage the malleoli bones 60. This configuration, in conjunction with padding 118 immediately above and below the malleoli 60, provides a snug fit in and around the area of the malleoli 60 without excess pressure. The wearer can adjust his or her foot within the ankle module 24 to the position where the malleoli 60 are most comfortably received. Thereafter, the anterior 36 and posterior 38 support straps can be fastened in order to securely retain the ankle module 24 in place.

FIG. 4 illustrates the feature of the present invention which provides improved proprioception. It can be seen that the posterior portion of the ankle module 24 provides a large opening 68 for the freedom of movement and protrusion of the calcaneus 58. That is, it has been found that the extreme posterior portion of the calcaneus 58 must preferably remain free and unrestricted, enjoying maximum contact with the shoe, and in turn, the ground. The open configuration of the present ankle brace 20, as illustrated in FIG. 4, provides this advantage. On the other hand, it is also important to control the anterior portion of the calcaneus 58 as it moves with the talus 56. It can be further noted from FIG. 4 that the direct and subtaloric control devices, 40 and 42, also extend in the posterior direction in order to provide taloric control, without inhibiting proprioception.

In this regard, it will be noted that the ankle module 24 of the present invention provides excellent tarsal joint 54 support without inhibiting the other portions of the foot. Thus, referring again to FIG. 2, it will be noted that the rear portion of the ankle module 24 is undercut at the lower region in order to open a large space 68 for the calcaneus 58. Moreover, the anterior portion of the ankle module 24 is somewhat truncated along the lower longitudinal regions so as to not interfere with the functioning of the metatarsal bones of the foot. Likewise, there is no attempt in the present ankle brace 20 to support the plantar arch region of the foot. This region and the metatarsals relate less directly to taloric control and yet complicate the goal of adjustability since these anatomical structures vary widely in individuals. Thus, the present ankle module 24 is designed to support the most critical portions of the ankle while leaving uninhibited the remainder of the foot.

FIGS. 3 and 4 illustrate the adjustability advantages of the present invention. One of the principal problems associated with prior ankle braces is that they either had to be custom-fit to the ankle of the user, in order to accommodate anatomical peculiarities, or they had to provide only minimal structural support in order to avoid interference with such peculiarities. Thus, an important advantage of the present invention is that it provides both excellent structural support for the ankle joint as well as a wide range of adjustability.

As illustrated in FIG. 6, an important advantage of the present invention is that the brace 20 accommodates both the ankle and the lower leg or shank portion of the wearer. As explained above, one means for supporting the tarsal joint 54 is provided by the support straps 28, 29, 36, 38, a pair of which is mounted both on the ankle module 24 as well as the calf module 22. In addition, however, the present invention is also provided with a two-piece adjustable calf design in order to accommodate leg dimensions of various users. In this design, two overlapping, interslidable arc members 74, 76 are integrated together with a latching mechanism 30 to create an essentially single structural member. An inner arc member 74 and an outer arc member 76 are shown in FIG. 6, which is a cross section of the calf module 22 taken through one of the latch mechanisms 30. The inner arc member 74 slides along the interior surface of the outer arc member 76 in order to provide adjustability for the girth or diameter of the user's shank. That is, if the inner arc member 74 and the outer arc member 76 are rotated relative to each other in the directions of the arrows 77 shown in FIG. 6, the calf module 22 will accommodate a smaller diameter shank. If the rotation is in the opposite direction of the arrows 77, a thicker leg is fittable.

The outer arc member 76 is provided with a pair of extending belt-like tabs 78 spaced apart from one another vertically which mate with an opening 80 in the latch mechanisms 30 on the inner arc member 74, as shown in the cross section of FIG. 6. Each latch mechanism 30 has a catch member 84 which extends perpendicularly within the opening 80. The tabs 78 of the outer arc member 76 are provided with multiple apertures 79 into which the catch member 84 may extend. If adjustability is necessary, the arc members 74, 76 can be rotated relative to one another to the appropriate position, and the catch member 84 secured in place in the nearest aperture 79 of the mating adjustment tab. The pair of combined tab 78 and latch mechanisms 30, therefore, provide a general adjustable sizing means for the calf module 22.

The stretchable support straps 28, 29 extending across the front vertical opening 23 of the calf module 22, on the other hand, provide a more sensitive adjustment mechanism for the calf module 22. Thus, any looseness that may result in the fit of the calf module 22 after the tabs 78 are in place in the latch mechanisms 30, can be taken up by the support straps 28, 29. Thus, the calf module 22 can be made to fit snugly around the shank of the user's leg. Moreover, these support straps 28, 29 extend through openings 86 in the vertical pillar 45 extending above the superior taloric control device 44. This configuration allows the support straps 28, 29 to more securely confine the arc members 74, 76 of the calf module 22 to their fitted relationship about the shank and to provide maximum support and stabilization to this portion of the leg. Thus, the calf module 22 on the shank, which has substantial leverage potential with respect to the tarsal joint 54, is carefully controlled so as to provide stability to the tarsal joint 54, thereby avoiding over-extension and further injury.

Besides adjustability, the ankle brace 20 of the present invention is also constructed so as to accommodate a wide variety of anatomical structures within a few standard sizes. For example, it is well known that foot sizes vary widely; however, shoes are manufactured in various sizes in order to fit virtually any foot. In this case, however, the ankle brace 20 must fit a portion of the foot as well as the shank portion of the user. This necessity complicates the goal of standardization for the present ankle brace 20. Nevertheless, it has been discovered that there is a certain rough correlation between certain characteristics of the ankle dimensions and the shank dimensions of most persons.

Figure 5:
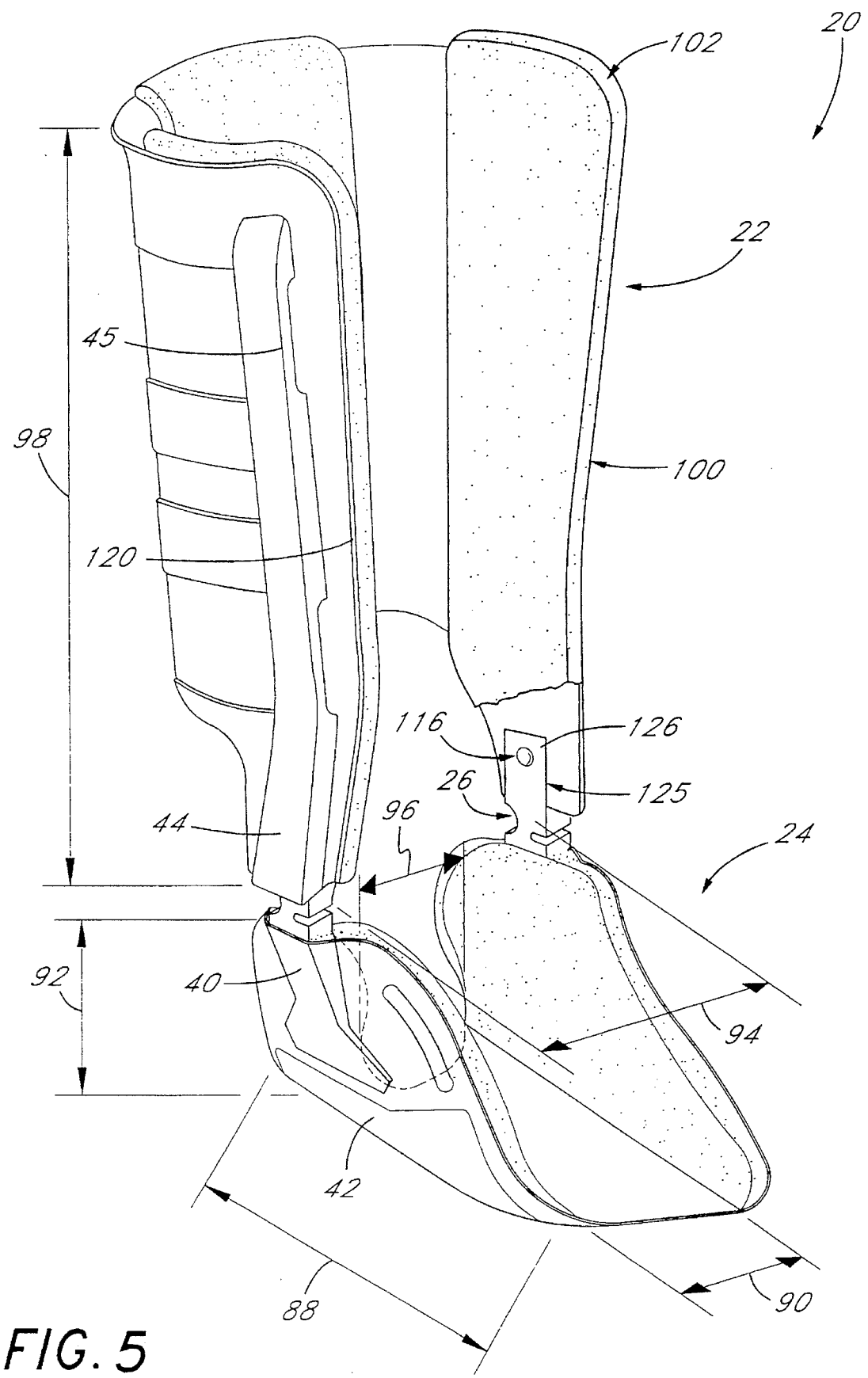
FIG. 5 is a perspective view of the ankle brace of the present invention, without the straps, illustrating the sizing parameters.

FIG. 5 illustrates certain parameters of the ankle module 24 of the present invention, including the sole length 88, the sole width 90, the hinge height 92, the hinge width 94, and the heel width 96. In the construction of the ankle brace 20 of the present invention, it has been found that these parameters correspond, within certain size ranges, to various parameters of the calf module 22, including the shank height 98, the mid circumference 100, and the top circumference 102, as illustrated in FIG. 5.

Thus, in order to simplify the purchase of the present invention by the consumer, these parameters are incorporated into the standard sizes of the ankle brace 20. For example, the present ankle brace 20 may be manufactured in standard small, medium, large, and extra large sizes. These sizes may correspond to standard men's shoe sizes as follows: small: sizes 5–6; medium: sizes 7–9; large: sizes 10–11; and extra large: sizes 12–13. The correlation between these standard men's shoe sizes and the ankle and calf module parameters described above and shown in FIG. 5 may be illustrated as follows:

| Ankle Brace Size | ANKLE MODULE | | | | |
| --- | --- | --- | --- | --- | --- |
| | Hinge Width | Hinge Height | Sole Width | Sole Length | Heel Width |
| S | 3" | 2½" | 2½" | 4" | 2⅜" |
| M | 3⅛" | 2⅞" | 2⅞" | 4⅛" | 2⅝" |
| L | 3½" | 3" | 3¼" | 4⅝" | 2⅞" |
| XL | 3¾" | 3½" | 3½" | 5⅛" | 3" |

CALF MODULE

| Ankle Brace Size | Mid Circumference | Top Circumference | Height |
| --- | --- | --- | --- |
| S | 10" | 10" | 6" |
| M | 10¾" | 12" | 6¼" |
| L | 11⅝" | 13½" | 6¾" |
| XL | 12" | 14½" | 7" |

However, it should be pointed out that these are only exemplary ranges of ankle and calf parameters and that other dimensions may be suitable and consistent with the present invention. Moreover, many principles of the present invention are compatible with ankle braces which are not necessarily adjustable, at least to the extent of the present invention.

FIGS. 7 and 8 illustrate the hinge 26 of the present invention which joins the calf module 22 to the ankle module 24. This hinge 26 permits relative freedom of the talocrural articulation about an imaginary horizontal axis, while restricting inversion and eversion which could cause reinjury.

The three principal components of the present hinge 26 comprise the upper connector 104, the lower connector 106, and a central pivot 108. The central pivot 108 comprises a pair of oppositely opposed flexion and extension stop devices, including a rear stop 112 which limits excessive downward extension and a front stop 110, which limits upward flexion. The central pivot 108 area is somewhat wider than the upper 104 and lower 106 connectors in order to provide a secure base for the front and rear stops 110, 112, and to prevent torsional rotation. In addition, the present hinge 26 is connected on the inside of the rigid control devices adjacent the hinge 26, wherein the hinge 26 is flush with the adjacent control devices, thereby eliminating the possibility of abrasion or irritation to the wearer. The upper and lower connectors 104, 106 are rectangular in shape, closely fitting and matching the rectangular shape of the recess 125 in the control devices. Their rectangular shape provides the connection with superior rotational and torsional resistance. Each connector is also provided with a hole 114, 126 for mounting the hinge 26 on the respective calf and ankle modules by means of fasteners 116 shown in FIG. 2 and 5.

It will be noted that the horizontal cross-sectional shape of this hinge 26 is generally rectangular. Thus, the moment of inertia of this device is such that it resists torsion, thereby protecting the ankle. Furthermore, the central pivot 108, while being similarly rectangular in cross section in order to resist torsion, allows a limited and normal range of movement by means of the cut-out portions which forms the stop devices. The longitudinal cross section of each connector 104, 106 is essentially trapezoidal, further resulting in restricted torsional movements.

As mentioned above in connection with FIGS. 3 and 4, the longitudinal cross section of the hinge 26 is generally arcuate in order to form a concave region on the interior surface 66 as illustrated in FIG. 8. This configuration forms part of the malleoli receptacles or cup-like areas 64 and accommodates those bones comfortably.

The present invention, besides providing excellent tarsal support and a wide range of flexibility, is also comfortable to wear. This advantage is provided by certain design features as illustrated in the various drawings. For example, as shown in FIG. 1, soft padding 118 is provided on the inner side 34 and bottom 32 surfaces of the ankle module 24 so as to avoid irritation to the wearer. The inner surfaces of the calf module 22 are also provided with a padding material 118, preferably comprised of a cellular plastic foam material with fabric laminate. This padding material 118 provides comfort as well as a secure and snug fit on the leg and ankle of the user.

In addition, many of the edges 120 of the ankle brace 20 of the present invention are thinned so as to be highly flexible. Thus, these edges 120 do not bite or dig into the skin of the user which may cause injury. Rather, the thinned down edges 120 of the device will easily roll or flux away from the skin in order to avoid injury. The support straps 36, 38 of the ankle module 24 are inserted through slots or openings 122 in this non-reinforced area. Thus, even though the support straps 36, 38 may be pulled snugly and fastened, the thinned edges 120 of the calf module 22 will bend away from the wearer's foot.

Thinned edges 120 are also provided along the periphery of the vertical opening 23 of the calf module 22, as shown in FIG. 5. Thus, the superior taloric control device 44 and the upwardly extending pillar 45 are positioned slightly behind the forward leading edge 120 of this calf module 22 opening 23. This provides rigidity to the calf module 22 while at the same time allows the leading edges 120 of the vertical opening 23 to be thin and flexible, as illustrated well in the cross-sectional view of FIG. 6. FIG. 6 also illustrates the thinned edges 120 of the inner arc member 74 which permits them to be flexible and to avoid injury to the user.

In conclusion, the present invention embodies several marked improvements over ankle braces of the prior art.

What is claimed is:

1. An ankle brace for use during physical activity, said ankle brace being adapted to be worn on a foot of a user and extend partway up the lower leg, said ankle brace comprising:

an upper member comprising plural arcuate submembers overlapping one another to provide an adjustable size opening for receiving the calf of the user;

a lower member adapted to receive the foot of the user;

a hinge connecting said upper member to said lower member to allow said members to flex with respect to one another, said hinge adapted to be positioned on said ankle brace adjacent the talus bone of the user; and at least a single taloric control device on at least one of said members in the region of the hinge for strengthening and supporting the talus bone in its various articulations, said taloric control device comprising lateral reinforcement areas disposed directly adjacent the hinge, slightly above the hinge, and slightly below the hinge, whereby injury to the ankle is inhibited.

2. The ankle brace of claim 1, wherein said lower member comprises two lower submembers, each of said lower submembers having at least one taloric control device located thereon and opposite one another, said lower submembers adapted to extend on either lateral side of the user's foot when said lower member receives said foot.

3. The ankle brace of claim 1, wherein the lower member comprises a pair of stabilizing members configured to be mounted on anterior and posterior sides of the hinge.

4. The ankle brace of claim 3, wherein said lower member comprises two lower submembers, said lower submembers adapted to extend on either lateral side of the user's foot when said lower member receives said foot, wherein said stabilizing members comprise adjustable straps mounted on said lower member, said adjustable straps adapted to securely couple said lower submembers over said foot.

5. An ankle brace for use during physical activity comprising:
   an upper member;
   a lower member adapted to extend below the upper member, said upper and lower members configured to be securely mounted on a foot of a user and extend partway up the lower leg;
   a hinge connecting said upper member to said lower member to allow said members to flex with respect to one another, whereby movement of the user is permitted, said hinge adapted to be positioned on said ankle brace adjacent the talus bone of the user; and
   at least a single taloric control device on at least one of said members located in the region of the hinge for strengthening and supporting the talus bone in its various articulations, said taloric control device comprising lateral reinforcement areas disposed directly adjacent the hinge, slightly above the hinge, and slightly below the hinge, whereby the articulations of the talus bone are supported in their movements and injury to the ankle is inhibited.

6. An ankle brace for use during physical activity, comprising:
   an upper member;
   a lower member adapted to extend below the upper member, said upper and lower members configured to be securely mounted on a foot of a user and extend partway up the lower leg;
   a hinge connecting said upper member to said lower member to allow said members to flex with respect to one another, whereby movement of the user is permitted, said hinge positioned on an ankle region of said ankle brace, said ankle region adapted to be positioned near the talus bone of the user; and
   at least a single taloric control device on at least one of said members located in the region of the hinge for strengthening and supporting the talus bone in its various articulations;
   said lower member comprising a pair of adjustable straps configured to be mounted on anterior and posterior regions of the ankle region of the ankle brace, said adjustable straps mounted on said lower member and adapted to securely mount said ankle region about the talus bone of the user, whereby injury to the talus bone is inhibited.

7. An ankle brace for use during physical activity, comprising:
   an upper member;
   a lower member;
   a hinge connecting said upper member to said lower member to allow said members to flex with respect to one another; and
   at least a single taloric control device on at least one of said members in the region of the hinge for strengthening and supporting the talus bone in its various articulations, said taloric control device comprising lateral reinforcement areas disposed directly adjacent the hinge, slightly above the hinge, and slightly below the hinge, whereby injury to the ankle is inhibited.

\* \* \* \* \*